US010555529B2

(12) United States Patent
Arimoto et al.

(10) Patent No.: US 10,555,529 B2
(45) Date of Patent: Feb. 11, 2020

(54) COMPOSITION FOR THE CONTROL OF GRAPEVINE ESCA DISEASE, BLACK DEAD ARM DISEASE, AND/OR EUTYPA DIEBACK DISEASE

(71) Applicant: RIKEN, Wako-shi, Saitama (JP)

(72) Inventors: Yutaka Arimoto, Wako (JP); Takayuki Kashima, Osaka (JP)

(73) Assignee: RIKEN, Wako-Shi, Saitama (JP)

( * ) Notice: Subject to any disclaimer, the term of this patent is extended or adjusted under 35 U.S.C. 154(b) by 0 days.

(21) Appl. No.: 15/574,192

(22) PCT Filed: May 18, 2016

(86) PCT No.: PCT/JP2016/064737
§ 371 (c)(1),
(2) Date: Nov. 15, 2017

(87) PCT Pub. No.: WO2016/186132
PCT Pub. Date: Nov. 24, 2016

(65) Prior Publication Data
US 2018/0125075 A1 May 10, 2018

(30) Foreign Application Priority Data

May 18, 2015 (JP) .................. 2015-101136

(51) Int. Cl.
*A01N 59/00* (2006.01)
*G01N 33/15* (2006.01)
*A01N 25/30* (2006.01)

(52) U.S. Cl.
CPC ............. *A01N 59/00* (2013.01); *G01N 33/15* (2013.01); *A01N 25/30* (2013.01)

(58) Field of Classification Search
None
See application file for complete search history.

(56) References Cited

U.S. PATENT DOCUMENTS

| | | | | | |
|---|---|---|---|---|---|
| 1,560,558 | A | * | 11/1925 | Fulton | A23B 7/157 424/715 |
| 3,056,721 | A | * | 10/1962 | Allais | A01N 59/20 424/631 |
| 5,443,835 | A | * | 8/1995 | Winston | A01N 25/30 424/405 |
| 5,496,568 | A | * | 3/1996 | Winston | A01N 25/24 424/715 |
| 6,284,286 | B1 | * | 9/2001 | Arimoto | A01N 25/30 424/682 |
| 2005/0129662 | A1 | * | 6/2005 | Lameri | A01N 25/02 424/93.4 |
| 2010/0292237 | A1 | | 11/2010 | Birner et al. | |
| 2013/0327678 | A1 | | 12/2013 | Zhang et al. | |
| 2015/0057156 | A1 | * | 2/2015 | Arimoto | A01N 37/04 504/306 |

FOREIGN PATENT DOCUMENTS

| | | | | |
|---|---|---|---|---|
| CN | 1356051 A | * | 7/2002 | |
| JP | 11-35404 A | | 2/1999 | |
| WO | WO 2007/110354 A2 | | 10/2007 | |
| WO | WO-2012052506 A1 | * | 4/2012 | ............... A01G 7/00 |
| WO | WO 2013/141381 A1 | | 9/2013 | |
| WO | WO 2015/044039 A1 | | 4/2015 | |

OTHER PUBLICATIONS

MR Sosnowski, AP Loschaivo, TJ Wicks, ES Scott. "Evaluating Treatments and Spray Application for the Protection of Grapevine Pruning Wounds from Infection by Eutypa lata." Plant Diseases, vol. 97 No. 12, Dec. 2013, pp. 1599-1604. (Year: 2013).*
BV Sivcev, IL Sivcev, ZZ Rankovic Vasic. "Plant Protection Products in Organic Grapevine Growing." Journal of Agricultural Sciences, vol. 55 No. 1, 2010, pp. 103-122. (Year: 2010).*
A Schilder. "Late-season fungicide sprays in grapes and potential effects on fermentation." https://www.canr.msu.edu/news/late_season_fungicide_sprays_in_grapes_and_potential_effects_on_fermentatio—accessed Feb. 14, 2019, published Sep. 23, 2011, pp. 1-3 (Year: 2011).*
Google Patents. English Translation of CN 1356051 A. https://patents.google.com/patent/CN1356051A/en?oq=potassiunn+carbonate+grape. Accessed by examiner Sep. 26, 2019, originally published Jul. 3, 2002, pp. 1-5. (Year: 2002).*
U.S. Department of Agriculture. "Potassium Bicarbonate—Technical Evaluation Report—Limited Scope." Obtained from https://www.ams.usda.gov/sites/default/files/media/Postassium%20Bicarbonate%20TR%202015.pdf on Nov. 27, 2019, originally published Jan. 22, 2015, pp. 1-11. (Year: 2015).*
International Search Report (PCT/ISA/210) dated Aug. 2, 2016, by the Japanese Patent Office as the International Searching Authority for International Application No. PCT/JP2016/064737.
Written Opinion (PCT/ISA/237) dated Aug. 2, 2016, by the Japanese Patent Office as the International Searching Authority for International Application No. PCT/JP2016/064737.
Anonymous: "Potassium Bicarbonate," Technical Evaluation Report—Limited Scope, Compiled by USDA, AMS, Agriculture Analytics Division for the USDA National Organic Program, Jan. 22, 2015, pp. 1-11 (11 pages).
Extended Search Report issued by the European Patent Office in corresponding European Patent Application No. 16796525.0-1110 dated Oct. 1, 2018 (7 pages).
The First Office Action issued by the State Intellectual Property Office of People's Republic of China in corresponding Chinese Patent Application No. 201680028755.X dated Sep. 12, 2019 (30 pages including partial English ranslation).
Agrios: "Plant Pathology, Fifth Edition," National Major Publishing Project, China Agricultural University Press, Mar. 2009 (8 pages including partial English translation).

* cited by examiner

*Primary Examiner* — Isaac Shomer
(74) *Attorney, Agent, or Firm* — Buchanan, Ingersoll & Rooney PC

(57) ABSTRACT

Provided is a composition for controlling at least one disease selected from grapevine ESCA disease, black dead arm, and Eutypa dieback disease, the composition containing at least one selected from the group consisting of alkali metal carbonates and alkali metal hydrogen carbonates as an active ingredient.

14 Claims, No Drawings

COMPOSITION FOR THE CONTROL OF GRAPEVINE ESCA DISEASE, BLACK DEAD ARM DISEASE, AND/OR EUTYPA DIEBACK DISEASE

TECHNICAL FIELD

The present invention relates to a composition for controlling grapevine ESCA disease, a method for controlling grapevine ESCA disease by applying the control composition, a method for identifying a grape infected with grapevine ESCA disease, and a searching method for an agent for controlling grapevine ESCA disease.

Moreover, the present invention also relates to a composition for controlling at least one disease selected from grapevine ESCA disease, black dead arm disease, and Eutypa dieback disease, and to a method for controlling at least one disease selected from grapevine ESCA disease, black dead arm disease, and Eutypa dieback disease by applying the control composition.

BACKGROUND ART

Grapevine ESCA disease, black dead arm disease, and Eutypa dieback disease (hereinafter may also be simply referred to as the subject diseases) are diseases which mainly occur in Europe, and known as major three diseases of grapevine trunk diseases in Europe.

Among the three diseases, the area where ESCA disease occurs is the largest, and ESCA disease is particularly regarded as a problem. On the other hand, recently, the area suffering from black dead arm disease has been rapidly expanding, bringing about a problem.

As to grapevine ESCA disease, it is believed that after the initial infection by *Phaeomoniella chlamydospora* or *Phaeoacremonium aleophilum*, one of wood-decay fungi such as *Fomitiporia punctata, F. mediterranea*, or *Stereum hirsutum* enters into the trunk from the infected site. As the decaying at the pathogen entry site, the discoloration and sponge-like formation of the vascular bundle, or the like gradually proceeds, the branches and leaves are supplied with less water and nutrients, eventually leading to the onset of symptoms such as leaf discoloration, dieback, and low fruiting. Thus, the grape production is significantly lowered. Grapevine ESCA disease is different from general diseases in that the ESCA disease onset is often seen in trees particularly grown to some extent for ten or more years. Since grape trees of ten or more years old can produce grapes having favorable taste, the economical damage, if any, to the producers could be great. Although sodium arsenite has been used as an effective chemical against the subject diseases, the use has been banned in many countries because of the toxicity problems to human, animals, and the environment. There is no effective measure at present.

The grapevine ESCA disease symptoms often appear after the decaying at the pathogen entry site inside the trunk gradually proceeds. In addition, except for several branches, all the other branches of a grape are cut off in winter. Accordingly, if a trunk portion near the remaining branches is infected with grapevine ESCA disease, the symptoms such as dieback and leaf discoloration are observed from the grape in the next year. Meanwhile, if the trunk portion near the remaining branches is not infected with grapevine ESCA disease, the symptoms may not appear in the grape in the next year. For these reasons, to identify a grape infected with grapevine ESCA disease, a follow-up examination is required for a long period, specifically at least three years.

Grapevine black dead arm disease is a new disease whose damage has become noticeable since this century. *Botryosphaeria parva* causes this disease. At the initial infection, a yellowish orange spot is observed like downy mildew, then leading to necrosis. This results in considerable influences on the grape production.

Grapevine Eutypa dieback disease is caused by *Eutypa lata*. The hypha growth rate of *Eutypa lata* is slow, but the grape growth is gradually retarded after the infection as in the case of ESCA disease, so that the production is significantly lowered. Although control is performed such as a microbicide treatment on the cross sections of branches after the pruning or incineration of damaged plants, only a limited effect is obtained.

Patent Literature 1 states that a plant disease control agent containing a biocidal inorganic compound, an amphoteric surfactant, and a nonionic surfactant and/or an anionic surfactant exhibits a control effect against a plant disease, specifically cucumber powdery mildew. However, there is no description or suggestion at all regarding grapevine ESCA disease.

Patent Literature 2 discloses that an agent for increasing a sugar content in a fruit of a plant, containing a compound represented by the formula MX (M represents alkali metal ion or alkaline earth metal ion, and X represents carbonate ion, hydrogen carbonate ion, acetate ion, citrate ion, succinate ion, phosphate ion, or pyrophosphate ion) as an active ingredient, remarkably increases the sugar content in a fruit of a plant, for example. However, there is no description at all regarding the control agent and the control method against the subject diseases.

Patent Literature 3 discloses a method for controlling grapevine ESCA disease by using an inhibitor of mitochondrial breathing chain at the level of b/c1 complex of plant pathogens. However, there is no description at all regarding the control agent of the present invention. Meanwhile, the control effect against grapevine ESCA disease is evaluated by examining the disease severity of shoots at each of four sub-stages of the growth stage. However, there is no description of the evaluation method of the present invention.

Patent Literature 4 describes a composition containing potassium hydrogen carbonate and an active ingredient selected from boscalid, pyrimethanil, metrafenone, cyprodinil, and fludioxinil. However, the control effect against the subject diseases is not demonstrated at all.

CITATION LIST

Patent Literatures

Patent Literature 1: Japanese Patent Application Publication No. Hei 11-35404
Patent Literature 2: International Publication No. WO2013/141381
Patent Literature 3: International Publication No. WO2007/110354
Patent Literature 4: International Publication No. WO2015/044039

SUMMARY OF INVENTION

Technical Problems

Grapevine ESCA disease is believed to be a complex disease caused by multiple pathogens. Since a control agent is less likely to physically reach inside the trunk where the pathogens exist, it is very difficult to control the disease.

Hence, there have been desires for the development of a control agent having an effect of suppressing the onset of grapevine ESCA disease symptoms.

In addition, grapevine black dead arm disease and Eutypa dieback disease, which are trunk diseases like grapevine ESCA disease, sometimes occur at the same time as ESCA disease. There have been desires for the development of a control agent effective against these diseases, too.

Moreover, the establishment of a method for identifying a grape infected with grapevine ESCA disease has been desired.

Further, the establishment of a test method capable of accurately evaluating an effect of a control agent against grapevine ESCA disease has been desired to efficiently select and develop a control agent.

Solution to Problems

To solve the above-described problems, the present inventors have conducted intensive studies. As a result, the inventors have found out that a composition containing at least one selected from the group consisting of alkali metal carbonates and alkali metal hydrogen carbonates has a high control effect against grapevine ESCA disease. Further, the inventors have found out that the growth rate (percentage increase) in a trunk circumference of a grape infected with grapevine ESCA disease is consistently low. This finding has revealed that it is possible to identify a grape infected with grapevine ESCA disease, and that it is possible to evaluate the control effect of a chemical to be tested against grapevine ESCA disease by comparison between a growth rate in a trunk circumference of a grape infected with grapevine ESCA disease to which the chemical to be tested is applied and a growth rate in a trunk circumference of a grape infected with grapevine ESCA disease but to which no chemical is applied. Thus, the present invention has been completed.

Moreover, the present inventors have conducted intensive studies to solve the problems. As a result, the inventors have found out that the composition containing at least one selected from the group consisting of alkali metal carbonates and alkali metal hydrogen carbonates has a high control effect against at least one disease selected from grapevine ESCA disease, grapevine black dead arm disease, and Eutypa dieback disease. This finding has led to the completion of the present invention.

Specifically, the present invention relates to: a composition for controlling grapevine ESCA disease (also referred to as agent for controlling grapevine ESCA disease), the composition comprising at least one alkali metal salt selected from the group consisting of alkali metal carbonates and alkali metal hydrogen carbonates as an active ingredient; and a method for controlling grapevine ESCA disease, the method comprising applying the control composition to a grape. Moreover, the present invention relates to a method for identifying a grape infected with grapevine ESCA disease, the method comprising comparing a percentage increase in a trunk circumference of a grape to be tested and a percentage increase in a trunk circumference of a grape not infected with grapevine ESCA disease to determine whether the grape to be tested is a plant infected with grapevine ESCA disease or not. Further, the present invention relates to a method for identifying a grape infected with grapevine ESCA disease, the method comprising comparing a percentage increase in a trunk circumference of a grape to which an agent for controlling grapevine ESCA disease is applied and a percentage increase in a trunk circumference of a grape to be tested to determine whether the grape to be tested is infected with grapevine ESCA disease or not. Furthermore, the present invention relates to a searching method for an agent for controlling grapevine ESCA disease, the method comprising comparing a percentage increase in a trunk circumference of a grape infected with grapevine ESCA disease to which a compound or composition to be tested is applied and a percentage increase in a trunk circumference of a grape infected with grapevine ESCA disease to which no chemical is applied to determine whether the compound or composition to be tested is an agent for controlling grapevine ESCA disease or not.

Furthermore, the present invention relates to: a composition for controlling at least one disease selected from grapevine ESCA disease, grapevine black dead arm disease, and Eutypa dieback disease, the composition comprising at least one alkali metal salt selected from the group consisting of alkali metal carbonates and alkali metal hydrogen carbonates as an active ingredient; and a method for controlling at least one disease selected from grapevine ESCA disease, grapevine black dead arm disease, and Eutypa dieback disease, the method comprising applying the control composition to a grape.

Advantageous Effects of Invention

The control composition and the control method of the present invention are very safe for the environment and the worker, and make it possible to suppress the onset of grapevine ESCA disease symptoms. Moreover, the identification method of the present invention makes it possible to identify a grape infected with grapevine ESCA disease within a shorter time than conventional methods. Further, the searching method of the present invention makes it possible to find out a chemical effective against grapevine ESCA disease by a simple process.

In addition, the control composition and the control method of the present invention are very safe for the environment and the worker, and make it possible to suppress the onset of symptoms of at least one disease selected from grapevine ESCA disease, grapevine black dead arm disease, and Eutypa dieback disease.

DESCRIPTION OF EMBODIMENTS

In this Description and Claims, to "control" grapevine ESCA disease refers to suppressing the onset of grapevine ESCA disease symptoms.

In this Description and Claims, to "control" at least one disease selected from grapevine ESCA disease, grapevine black dead arm disease, and Eutypa dieback disease refers to suppressing the onset of symptoms of at least one disease selected from grapevine ESCA disease, grapevine black dead arm disease, and Eutypa dieback disease.

The control composition of the present invention is capable of suppressing the onset of grapevine ESCA disease symptoms. Specifically, the control composition of the present invention is capable of suppressing: the onset of grapevine ESCA disease symptoms in a grape infected with grapevine ESCA disease; and/or the infection of a grape with grapevine ESCA disease and the onset of symptoms thereof, the grape not having been infected with grapevine ESCA disease. Thus, the control composition of the present invention is usable as an agent for suppressing the onset of grapevine ESCA disease symptoms, too. The grapevine ESCA disease symptoms include leaf discoloration, leaf withering, low fruiting, and the like.

The control composition of the present invention is capable of suppressing the onset of symptoms of at least one disease selected from grapevine ESCA disease, grapevine black dead arm disease, and Eutypa dieback disease. Specifically, the control composition of the present invention is capable of suppressing: the onset of symptoms of at least one disease selected from grapevine ESCA disease, grapevine black dead arm disease, and Eutypa dieback disease in a grape infected with at least one disease selected from grapevine ESCA disease, grapevine black dead arm disease, and Eutypa dieback disease; and/or the infection of a grape with at least one disease selected from grapevine ESCA disease, grapevine black dead arm disease, and Eutypa dieback disease and the onset of symptoms thereof, the grape not having been infected with at least one disease selected from grapevine ESCA disease, grapevine black dead arm disease, andEutypadiebackdisease. Thus, the control composition of the present invention is usable as an agent for suppressing the onset of symptoms of at least one disease selected from grapevine ESCA disease, grapevine black dead arm disease, and Eutypa dieback disease, too. The symptoms of at least one disease selected from grapevine ESCA disease, grapevine black dead arm disease, and Eutypa dieback disease include leaf discoloration, leaf withering, low fruiting, and the like.

The control composition and the control method of the present invention is characterized in that at least one alkali metal salt selected from the group consisting of alkali metal carbonates and alkali metal hydrogen carbonates is incorporated as an active ingredient. The alkali metal is preferably potassium or sodium, and more preferably potassium.

The alkali metal salt includes potassium carbonate, sodium carbonate, potassium hydrogen carbonate, sodium hydrogen carbonate, and the like. Potassium carbonate, potassium hydrogen carbonate, and sodium hydrogen carbonate are preferable. The alkali metal salt is more preferably potassium carbonate and potassium hydrogen carbonate, and particularly preferably potassium hydrogen carbonate.

Each of the alkali metal salts may be used alone, or may be used in mixture. Each of potassium carbonate or potassium hydrogen carbonate is preferably used alone.

The content of the alkali metal salt in the control composition is preferably 50% by mass or more, the content is more preferably 60% by mass or more, the content is further preferably 70% by mass to 95% by mass, the content is furthermore preferably 75% by mass to 90% by mass, the content is still further preferably 75% by mass to 85% by mass, and the content is yet still further preferably 80% by mass to 85% by mass. In addition, the content of the control agent of the present invention in the control composition may be 100% by mass.

The control composition of the present invention preferably further contains a vegetable oil and/or a surfactant.

The vegetable oil includes soybean oil, sunflower oil, olive oil, kapok oil, castor oil, palm oil, camellia oil, coconut oil, sesame oil, corn oil, rice bran oil, peanut oil, cottonseed oil, rapeseed oil, linseed oil, tung oil, and the like. The vegetable oil is preferably soybean oil and sunflower oil, and more preferably soybean oil.

Each of the vegetable oils may be used alone, or may be used in mixture. The content of the vegetable oil relative to the total amount of the composition of the present invention is preferably 0.001 to 50% by mass, more preferably 0.01 to 40% by mass, further preferably 0.1 to 30% by mass, furthermore preferably 1 to 25% by mass, still further preferably 1 to 20% by mass, yet still further preferably 1 to 10% by mass, and yet still furthermore preferably 1 to 5% by mass. Moreover, in the case where soybean oil is used as the vegetable oil, the content of the soybean oil relative to the total amount of the composition of the present invention is preferably 0.1 to 10% by mass, and more preferably 1 to 5% by mass. In the case where sunflower oil is used as the vegetable oil, the content of the sunflower oil relative to the total amount of the composition of the present invention is preferably 0.1 to 20% by mass, and more preferably 1 to 20% by mass.

In the composition of the present invention, the mixing ratio of the alkali metal salt to the vegetable oil by mass is normally preferably 1:1000 to 1000:1, more preferably 1:100 to 100:1, further preferably 1:10 to 50:1, furthermore preferably 1:1 to 40:1, still further preferably 3:1 to 30:1, yet still further preferably 10:1 to 30:1, and yet still furthermore preferably 15:1 to 25:1.

The surfactant includes nonionic surfactants, cationic surfactants, anionic surfactants, and the like. Among these, the surfactant preferably includes a nonionic surfactant, and more preferably consists of a nonionic surfactant.

Examples of the nonionic surfactant include sorbitan fatty acid ($C_{8-18}$) esters (specifically, sorbitanmonostearate, sorbitan monopalmitate, sorbitan monooleate, sorbitol monolaurate, and the like), glycerin fatty acid ($C_{8-18}$) esters (specifically, glycerol monostearate, glycerol monooleate, and the like), propylene glycol fatty acid ($C_{8-18}$) esters (specifically, propylene glycol monostearate, propylene glycol monooleate, propylene glycol monopalmitate, and the like), sucrose fatty acid ($C_{8-18}$) esters (specifically, sucrose stearic acid ester, sucrose palmitic acid ester, sucrose myristic acid ester, sucrose oleic acid ester, sucrose lauric acid ester, sucrose behenic acid ester, and the like), polyglycerin fatty acid ($C_{8-18}$) esters (specifically, diglycerin monooleate, diglycerin monostearate, decaglycerin monolaurate, decaglycerin monooleate, fatty acid polyglycerides, and the like), organic acid monoglycerides (specifically, acetic acid monoglyceride, lactic acid monoglyceride, citric acid monoglyceride, diacetyl tartaric acid monoglyceride, succinic acid monoglyceride, and the like), fatty acid alcohol polyglycol ethers, acetylene glycols, acetylene alcohols, oxyalkylene block polymers, polyoxyethylene ($C_{8-18}$) alkyl ethers (specifically, polyoxyethylene lauryl ether and the like), polyoxyethylene alkylaryl ethers, polyoxyethylene styrylaryl ethers, polyoxyethylene glycol alkyl ethers, polyoxyethylene fatty acid esters (specifically, polyoxyethylene glycol monolaurate, polyoxyethylene glycol monostearate, polyoxyethylene glycol monooleate, and the like), polyoxyethylene sorbitan fatty acid ($C_{8-18}$) esters (specifically, polyoxyethylene sorbitan monolaurate, polyoxyethylene sorbitan monopalmitate, polyoxyethylene monostearate, polyoxyethylene sorbitan monooleate, and the like), polyoxyethylene sorbitol fatty acid esters (specifically, polyoxyethylene sorbitol tetraoleate and the like), polyoxyethylene glycerin fatty acid esters (specifically, polyoxyethylene glyceryl monostearate, polyoxyethylene glyceryl oleate, and the like), polyoxyethylene hydrogenated castor oil, polyoxyethylene castor oil, polyoxypropylene fatty acid esters, and the like, and polyoxyethylene alkylamines (specifically, polyoxyethylene cocoamine and the like). Among these, preferable are polyglycerin fatty acid ($C_{8-18}$) esters, polyoxyethylene ($C_{8-18}$) alkyl ethers, polyoxyethylene sorbitan fatty acid ($C_{8-18}$) esters, and polyoxyethylene alkylamines (specifically, polyoxyethylene cocoamine and the like). More specifically, preferable are diglycerin monooleate (for example, Poem DO-100V (product name, manufactured by Riken Vitamin Co., Ltd.), NIKOL DGMO-90V (product name, Nippon Surfactant Industries Co., Ltd.), and so forth), polyoxyethylene lauryl ether (for example, Rikemal B-205 (product name, manufactured by Riken Vitamin Co., Ltd.), Pegnol TH-8 (product name, manufactured by Toho Chemical Industry Co., Ltd.), Synperonic L11 (product name, manufactured by CRODA International plc), and so forth) and polyoxyethylene sorbitan monolaurate (for example, Sorbon T-20 (product name, manufactured by Toho Chemical Industry Co., Ltd.), Tween 20 (product name, manufactured by CRODA International plc), Tween 21 (product name, manufactured by CRODA International plc), and so forth), and polyoxyethylene cocoamine (for example, Sorpol 7643 (product name, manufactured by Toho Chemical Industry Co., Ltd.), Genamin C020 (product name, manufactured by CLARIANT)). Among these, preferable is at least one selected from the group consisting of polyglycerin fatty acid ($C_{8-18}$) esters, polyoxyethylene ($C_{8-18}$) alkyl ethers, polyoxyethylene sorbitan fatty acid ($C_{8-18}$) esters, and polyoxyethylene alkylamines (specifically, polyoxyethylene cocoamine and the like); more preferable is at least one selected from the group consisting of diglycerin monooleate, polyoxyethylene lauryl ether, polyoxyethylene sorbitan monolaurate, and polyoxyethylene cocoamine.

The cationic surfactants include alkoxylated aliphatic amines, alkylamine salts (specifically, coconut amine acetate, stearyl amine acetate, and the like), quaternary ammonium salts (specifically, lauryl trimethyl ammonium chloride, stearyl trimethyl ammonium chloride, and the like), and the like. Genamin C100 (product name, manufactured by CLARIANT), and the like) are preferable.

Examples of the anionic surfactants include fatty acid salts, benzoates, alkyl sulfosuccinates, dialkyl sulfosuccinates, alkyl sulfuric acid ester salts, alkyl sulfates, alkyl diglycol ether sulfates, alcohol sulfuric acid ester salts, alkyl sulfonates, lignin sulfonates, alkyl diphenyl ether disulfonates, polystyrene sulfonates, alkyl phosphoric acid ester salts, alkylaryl phosphates, styrylaryl phosphates, polyoxyethylene alkyl ether sulfuric acid ester salts, polyoxyethylene alkylaryl ether sulfates, polyoxyethylene styrylaryl ether sulfates, ammonium salts of polyoxyethylene styrylaryl ether sulfates, polyoxyethylene alkylaryl ether sulfuric acid ester salts, polyoxyethylene alkyl ether phosphates, polyoxyethylene alkylaryl phosphoric acid ester salts, polyoxyethylene styrylaryl ether phosphoric acid esters or salts thereof, and the like.

As the surfactant, one of the surfactants may be used alone, or two or more of the surfactants may be used in combination. The content of the surfactant relative to the total amount of the composition of the present invention is preferably 0.001 to 50% by mass, more preferably 0.01 to 40% by mass, further preferably 0.1 to 30% by mass, furthermore preferably 1 to 20% by mass, still further preferably 5 to 15% by mass, and yet still further preferably 10 to 15% by mass.

In the composition of the present invention, the mixing ratio of the alkali metal salt to the surfactant by mass is normally preferably 1:1000 to 1000:1, more preferably 1:100 to 100:1, further preferably 1:10 to 50:1, furthermore preferably 1:5 to 30:1, still further preferably 1:1 to 30:1, still furthermore preferably 1:1 to 15:1, yet still further preferably 2:1 to 10:1, and yet still furthermore preferably 4:1 to 8:1.

Additionally, the composition of the present invention may contain an adjuvant such as a carrier and an oil absorber as necessary.

Examples of the carrier include diatomaceous earth, slaked lime, talc, white carbon, bentonite, starches, sugars such as lactose and fructose, succinic acid, malic acid, citric acid, ferric citrate, lactic acid, tartaric acid, phosphoric acid, potassium acetate, tetrapotassium pyrophosphate, monopotassium citrate, dipotassium citrate, potassium hydrogen tartrate, potassium phosphate, potassium dihydrogen phosphate, dipotassium hydrogen phosphate, tripotassium phosphate, potassium metaphosphate, potassium nitrate, sodium chloride, sodium acetate, sodium sulfate, sodium dihydrogen pyrophosphate, tetrasodium pyrophosphate, sodium succinate, disodium succinate, sodium malate, trisodium citrate, sodium ferrous citrate, sodium lactate, sodium phosphate, sodium dihydrogen phosphate, disodium hydrogen phosphate, trisodium phosphate, sodium metaphosphate, sodium nitrate, calcium chloride, calcium sulfate, calcium dihydrogen pyrophosphate, calcium citrate, calcium lactate, calcium carbonate, calcium phosphate, calcium dihydrogen phosphate, calcium monohydrogen phosphate, tricalcium phosphate, ammonium chloride, ammonium sulfate, ammonium ferric citrate, ammonium carbonate, ammonium hydrogen carbonate, ammonium phosphate, ammonium dihydrogen phosphate, diammonium hydrogen phosphate, magnesium chloride, magnesium sulfate, magnesium carbonate, ferric chloride, ferrous sulfate, ferrous pyrophosphate, iron lactate, copper sulfate, and the like.

As the carrier, one of the carriers may be used alone, or two or more of the carriers may be used in combination. The content of the carrier is not particularly limited, and the carrier can be used within such a range that the effects of the present invention are not impaired. For example, the carrier may be incorporated in an amount of 0 to 10% by mass or 0.1 to 10% by mass relative to the total amount of the composition of the present invention.

Examples of the oil absorber include silicon dioxide, starch hydrolysates, kaoline, clay, diatomaceous earth, calcium silicate, acid clay, carbon black, processed perlite (pearl stone), ultrafine particles of anhydrous aluminum oxide, ultrafine particles of titanium oxide, basic magnesium carbonate, magnesium aluminosilicate, silica-alumina synthetic fillers, hydrous magnesium silicate, and the like.

As the oil absorber, one of the oil absorbers may be used alone, or two or more of the oil absorbers may be used in combination. The content of the oil absorber is not particularly limited, and the oil absorber can be used within such a range that the effects of the present invention are not impaired. For example, the oil absorber may be incorporated in an amount of 0 to 50% by mass, 0.1 to 50% by mass, 0.1 to 30% by mass, 0.1 to 20% by mass, or 0.1 to 10% by mass, relative to the total amount of the composition of the present invention.

The control composition of the present invention may be in a form of powder, wettable powder, water dispersible granule, granule, water-based suspension, oil-based suspension, water soluble powder, emulsion, liquid, paste, aerosol, ultra-low volume formulation, or the like.

The alkali metal carbonates and the alkali metal hydrogen carbonates, which serve as the active ingredient, are hardly dissolved in a vegetable oil and a surfactant. Accordingly, in the case where the composition contains a vegetable oil and/or a surfactant, it is difficult to handle the composition in some cases; for example, the active ingredient is likely to precipitate during the storage, and it is not easy to disperse the precipitate again. Adjusting the particle diameter of the alkali metal salt incorporated in the composition makes it possible to improve the handling difficulty. The particle diameter preferably ranges from, in terms of sieve opening, 0.038 mm (400 mesh/Tyler) to 2.0 mm (9 mesh/Tyler), and the particle diameter more preferably ranges from 0.045 mm (325 mesh/Tyler) to 1.7 mm (10 mesh/Tyler).

In the case where potassium hydrogen carbonate or potassium carbonate is used as the alkali metal salt, the particle diameter preferably ranges from, in terms of sieve opening, 0.075 mm (200 mesh/Tyler) to 2.0 mm (9 mesh/Tyler), and the particle diameter more preferably ranges from 0.09 mm (170 mesh/Tyler) to 1.7 mm (10 mesh/Tyler). In the case where sodium hydrogen carbonate or sodium carbonate is used, the particle diameter preferably ranges from, in terms of sieve opening, 0.038 mm (400 mesh/Tyler) to 2.0 mm (9 mesh/Tyler), the particle diameter more preferably ranges from 0.045 mm (325 mesh/Tyler) to 1.7 mm (10 mesh/Tyler), and the particle diameter further preferably ranges from 0.045 mm (325 mesh/Tyler) to 0.15 mm (100 mesh/Tyler).

In addition, the composition of the present invention may be in a form of package in which the composition is packaged in a water soluble film, for example, in a form of water soluble pack or the like. This makes it possible to greatly improve the handling difficulty. The mass of the water soluble pack may be changed as appropriate depending on the application amount, but is normally 10 to 10000 g, preferably 100 to 5000 g.

The material of the water soluble film used in the water soluble pack should be one that is not influenced by the alkaline active ingredient, and when added into water, dissolved therein quickly, for example, within appropriately 1 hour immediately after the addition. Examples of the material include polyvinyl alcohols, polyethylene glycols, modified polyvinyl alcohols, water-soluble vinylons, water-soluble dextrins, carboxymethyl celluloses, hydroxyethyl cellulose, methyl celluloses, alginates, gelatins, pectins, pullulans, polyvinylpyrrolidones, polyacrylates, polyethylene oxides, starches, and the like. Preferable are polyvinyl alcohols and polyethylene glycols, and more preferable are polyvinyl alcohols.

The water soluble film should have such a thickness that the vegetable oil in the composition for controlling grapevine ESCA disease does not bleed out during the storage. The thickness is preferably 10 to 100 μm, and more preferably 20 to 80 μm.

When the composition of the present invention is applied, the treatment thereof can be performed in combination with other agricultural chemicals, for example, a microbicide, an insecticide, a miticide, a nematicide, a soil pesticide, an antiviral agent, an attractant, a herbicide, a plant growth regulator, and the like.

In the other agricultural chemicals, active ingredient compounds (common names or test codes of Japan Plant Protection Association) of the microbicide can be selected as appropriate, for example, from the following compound group. Even though not particularly mentioned herein, if these compounds have salts, alkyl esters, various structural isomers such as optical isomers, and the like, these are also included as a matter of course.

anilinopyrimidine-based compounds such as mepanipyrim, pyrimethanil, and cyprodinil;

triazolopyrimidine-based compounds such as 5-chloro-7-(4-methylpiperidin-1-yl)-6-(2,4,6-trifluropheny 1) [1,2,4]triazoro[1,5-a]pyrimidine;

pyridinamine-based compounds such as fluazinam;

azole-based compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, azaconazole, triticonazole, imazalil, ipfentrifluconazole, and mefentrifluconazole;

quinoxaline-based compounds such as quinomethionate;

dithiocarbamate-based compounds such as maneb, zineb, mancozeb, polycarbamate, metiram, propineb, and thiram;

organochloride-based compounds such as fthalide, chlorothalonil, and quintozene;

imidazole-based compounds such as benomyl, thiophanate-methyl, carbendazim, thiabendazole, and fuberiazole;

cyanoacetamide-based compounds such as cymoxanil;

anilide-based compounds such as metalaxyl, metalaxyl-M (a.k.a. mefenoxam), oxadixyl, ofurace, benalaxyl, benalaxyl-M (a.k.a. kiralaxyl, chiralaxyl), furalaxyl, cyprofuram, carboxin, oxycarboxin, thifluzamide, boscalid, bixafen, isotianil, tiadinil, sedaxane, and pyraziflumid;

sulfamide-based compounds such as dichlofluanid;

copper-based compounds such as cupric hydroxide, oxine copper, anhydrous copper sulfate, copper nonylphenolsulfonate, copper 8-hydroxyquinoline, and dodecyl benzenesulfonate bisethylene diamine copper complex salt (II) (a.k.a. DBEDC);

organophosphorus-based compounds such as fosetyl-aluminum (fosetyl-Al), tolclofos-methyl, edifenphos, and iprobenfos;

phthalimide-based compounds such as captan, captafol, and folpet;

dicarboximide-based compounds such as procymidone, iprodione, and vinclozolin;

benzanilide-based compounds such as flutolanil, mepronil, and benodanil;

amide-based compounds such as penthiopyrad, penflufen, furametpyr, isopyrazam, silthiopham, fenoxanil, fenfuram, fluxapyroxad, and benzovindiflupyr;

benzamide-based compounds such as fluopyram and zoxamide;

thiophene amide-based compounds such as isofetamid;

piperazine-based compounds such as triforine;

pyridine-based compounds such as pyrifenox and pyrisoxazole;

carbinol-based compounds such as fenarimol and nuarimol;

piperidine-based compounds such as fenpropidin;

morpholine-based compounds such as fenpropimorph and tridemorph;

organotin-based compounds such as fentin hydroxide and fentin acetate;

urea-based compounds such as pencycuron;

carboxamide-based compounds such as dimethomorph, flumorph, pyrimorph, iprovalicarb, benthiavalicarb-isopropyl, valifenalate, and mandipropamid;

phenylcarbamate-based compounds such as diethofencarb;

cyanopyrrole-based compounds such as fludioxonil and fenpiclonil;

strobilurin-based compounds such as azoxystrobin, kresoxim-methyl, metominostrobin, trifloxystrobin, picoxystrobin, oryzastrobin, dimoxystrobin, pyraclostrobin, fluoxastrobin, Enestroburin, Pyraoxystrobin, Pyrametostrobin, coumoxystrobin, enoxastrobin, fenaminstrobin, flufenoxystrobin, triclopyricarb, and mandestrobin;

oxazolidinone-based compounds such as famoxadone;

thiazolecarboxamide-based compounds such as ethaboxam;

imidazolinone-based compounds such as fenamidone;

hydroxyanilide-based compounds such as fenhexamid;

benzene sulfonamide-based compounds such as flusulfamide;

oxime ether-based compounds such as cyflufenamid;

anthraquinone-based compounds such as dithianon;

crotonic acid-based compounds such as meptyldinocap;

antibiotics such as validamycin, kasugamycin, and polyoxins;

guanidine-based compounds such as iminoctadine and dodine;

quinoline-based compounds such as tebufloquin, quinoxyfen, and quinofumelin;

thiazolidine-based compounds such as flutianil;

carbamate-based compounds such as propamocarb hydrochloride and tolprocarb;

sulfonamide-based compounds such as amisulbrom and cyazofamiid;

aryl phenyl ketone-based compounds such as metrafenone and pyriofenone;

sulfur-based compounds such as sulfur and lime sulfur;

other compounds such as pyribencarb, isoprothiolane, pyroquilon, diclomezine, chloropicrin, dazomet, metam-sodium, nicobifen, diclocymet, proquinazid, mandipropamid, fluopicolide, carpropamid, ferimzone, spiroxamine, fenpyrazamine, ametoctradin, oxathiapiprolin, picarbutrazox, dipymetitrone, pyraziflumid, SB-4303, BAF-1107, and SYJ-247;

microbial microbicides such as *Bacillus amyloliqefaciens* strain QST713, *Bacillus amyloliqefaciens* strain FZB24, *Bacillus amyloliqefaciens* strain MBI600, *Bacillus amyloliqefaciens* strain D747, *Pseudomonas fluorescens*, *Bacillus subtilis*, and *Trichoderma atroviride* SKT-1; and plant extracts such as tea tree oil.

In the other agricultural chemicals, active ingredient compounds (common names or test codes of Japan Plant Protection Association) of the insecticide, miticide, nematicide, or soil pesticide, in other words, pesticides, can be selected as appropriate, for example, from the following compound group. Even though not particularly mentioned herein, if these compounds have salts, alkyl esters, various structural isomers such as optical isomers, and the like, these are also included as a matter of course.

organophosphate-based compounds such as profenofos, dichlorvos, fenamiphos, fenitrothion, EPN ((RS)—(O-ethyl O-4-nitrophenyl phenylphosphonothioate)), diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, oxydeprofos (a.k.a. ESP), azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, and phorat;

carbamate-based compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC (3,5-xylyl methylcarbamate), and fenothiocarb;

nereistoxin derivatives such as cartap, thiocyclam, thiocyclam hydrogen oxalate (thiocyclam oxalate), thiocyclam hydrochloride, bensultap, thiosultap, monosultap (a.k.a. thiosultap-monosodium), bisultap (a.k.a. thiosultap-disodium), and polythialan;

organochloride-based compounds such as dicofol, tetradifon, endosulfan, dienochlor, and dieldrin;

organometallic compounds such as fenbutatin oxide and cyhexatin;

pyrethroid-based compounds such as fenvalerate, permethrin, cypermethrin, alpha-cypermethrin, zeta-cypermethrin, theta-cypermethrin, beta-cypermethrin, deltamethrin, cyhalothrin, gamma-cyhalothrin, lambda-cyhalothrin, tefluthrin, kappa-tefluthrin, ethofenprox, flufenprox, cyfluthrin, beta-cyfluthrin, fenpropathrin, flucythrinate, fluvalinate, cycloprothrin, pyrethrins, esfenvalerate, tetramethrin, resmethrin, protrifenbute, bifenthrin, kappa-bifenthrin, acrinathrin, allethrin, tau-fluvalinate, tralomethrin, profluthrin, metofluthrin, heptafluthrin, phenothrin, flumethrin, momfluorothrin, and silafluofen;

benzoylurea-based compounds such as diflubenzuron, chlorfluazuron, teflubenzuron, flufenoxuron, lufenuron, novaluron, triflumuron, hexaflumuron, bistrifluron, noviflumuron, and fluazuron;

juvenile hormone-like compounds such as methoprene, pyriproxyfen, fenoxycarb, and diofenolan;

pyridazinone-based compounds such as pyridaben;

pyrazole-based compounds such as fenpyroximate, fipronil, tebufenpyrad, ethiprole, tolfenpyrad, acetoprole, pyrafluprole, pyriprole, cyenopyrafen, pyflubumide, and flufiprole;

neonicotinoid-based compounds such as imidacloprid, nitenpyram, acetamiprid, thiacloprid, thiamethoxam, clothianidin, nidinotefuran, dinotefuran, and nithiazine;

hydrazine-based compounds such as tebufenozide, methoxyfenozide, chromafenozide, and halofenozide;

pyridine-based compounds such as pyridalyl and flonicamid;

cyclic ketoenol-based compounds such as spirodiclofen, spiromesifen, and spirotetramat;

strobilurin-based compounds such as fluacrypyrim and pyriminostrobin;

pyrimidinamine-based compounds such as flufenerim and pyrimidifen;

organosulfur compounds such as malathion;

urea-based compounds such as flufenoxuron;

triazine-based compounds such as cyromazine;

hydrazone-based compounds such as hydramethylnon;

diamide-based compounds such as flubendiamide, chlorantraniliprole, cyantraniliprole, cyclaniliprole, tetraniliprole, and broflanilide;

thiourea-based compounds such as diafenthiuron and chloromethiuron;

formamidine-based compounds such as amitraz, chlordimeform, and chloromebuform; and other compounds including such compounds as buprofezin, hexythiazox, triazamate, pymetrozine, chlorfenapyr, indoxacarb, acequinocyl, etoxazole, 1,3-dichloropropene, benclothiaz, bifenazate, propargite, clofentezine, metaflumizone, cyflumetofen, pyrifluquinazone, fenazaquin, amidoflumet, sulfluramid, hydramethylnon, metaldehyde, sulfoxaflor, fluensulfone, verbutin, dicloromezotiaz, triflumezopyrim, fluhexafon, tioxazafen, afidopyropen, flometoquin, and flupyradifurone.

Furthermore, the composition of the present invention may be applied in combination with the following compounds.

microbial agricultural chemicals such as *Bacillus thuringiensis aizawai, Bacillus thuringiensis kurstaki, Bacillus thuringiensis israelensis, Bacillus thuringiensis japonensis*, and *Bacillus thuringiensis tenebrionis*, or crystalline protein toxins produced by *Bacillus thuringiensis*, entomopathogenic viruses, entomopathogenic filamentous fungi, and nematophagous filamentous fungi;

antibiotics and semi-synthetic antibiotics such as avermectin, emamectin benzoate, milbemectin, milbemycin, spinosad, ivermectin, lepimectin, abamectin, emamectin, and spinetoram;

natural products such as azadirachtin, rotenone, and ryanodine;

repellents such as deet; and physical control agents such as paraffin oil and mineral oil.

The present invention also includes a method for controlling grapevine ESCA disease, characterized in that the method includes applying the composition of the present invention to a grape. Moreover, the present invention also includes a method for controlling at least one disease selected from grapevine ESCA disease, grapevine black dead arm disease, and Eutypa dieback disease, characterized in that the method includes applying the composition of the present invention to a grape. The composition of the present invention can be applied to a cane, leaf, and trunk present in a bunch zone of a grape tree, or soil around the grape tree. The term bunch zone refers to a range around a fruit-bearing portion in the upper part of a grape, and is a portion crowded with grape fruits, leaf, and shoot (cane). The application amount varies depending on the differences in the growing conditions, use method, formulation form, and so forth, and cannot be generally specified. Nevertheless, in the cases of the application to cane, leaf, and trunk in a bunch zone, at least one selected from the group consisting of alkali metal carbonates and alkali metal hydrogen carbonates is preferably applied in an amount of 0.01 to 1000 kg/ha, and more preferably applied in an amount of 0.1 to 100 kg/ha. In the case of the application to soil, at least one selected from the group consisting of alkali metal carbonates and alkali metal hydrogen carbonates is preferably applied in an amount of 0.01 to 1000 kg/ha, more preferably applied in an amount of 0.1 to 100 kg/ha, further preferably applied in an amount of 1 to 100 kg/ha, furthermore preferably applied in an amount of 2 to 50 kg/ha, and particularly preferably applied in an amount of 5 to 25 kg/ha. The application timing is not particularly limited, and includes before and after the pruning timing, and before and after the optimum harvest date. The application timing is preferably before and after the optimum harvest date, more preferably a period between eight weeks before the harvest and eight weeks after the harvest, and particularly preferably a period between four weeks before the harvest and four weeks after the harvest.

In a case where the composition of the present invention is diluted for use, the composition can be diluted for use, for example, 1 to 500-fold, preferably 3 to 300-fold, more preferably 5 to 200-fold, and further preferably 20 to 100-fold, by using a diluent such as water.

The number of the applications performed is not particularly limited, and the application is preferably performed at least once, more preferably performed at least once per year, further preferably performed one to ten times per year, more preferably performed one to five times per year, furthermore preferably performed two to five times per year, and still further preferably performed three to five times.

The composition of the present invention can be applied by normally employed application methods in general, that is, scattering (for example, scattering, spraying, misting, atomizing, granular-form application, and so forth), soil applications (mixing, drenching, and so forth), surface applications (coating, powder dressing, covering, and so forth), and other methods.

Another embodiment of the present invention is a method for identifying a grape infected with grapevine ESCA disease, the method including the step of comparing a percentage increase in a trunk circumference of a grape to be tested and a percentage increase in a trunk circumference of a grape not infected with grapevine ESCA disease to determine whether the grape to be tested is infected with grapevine ESCA disease or not.

If a grape to be tested is infected with grapevine ESCA disease, the percentage increase in a trunk circumference thereof is smaller than the percentage increase in a trunk circumference of a grape not infected with grapevine ESCA disease. This enables one to determine whether a grape to be tested is infected with grapevine ESCA disease or not.

Thus, the above identification method is preferably a method for identifying a grape infected with grapevine ESCA disease, the method including the step of comparing a percentage increase in a trunk circumference of a grape to be tested and a percentage increase in a trunk circumference of a grape not infected with grapevine ESCA disease to determine that the grape to be tested is infected with grapevine ESCA disease if the ratio of the percentage increase in the trunk circumference of the grape to be tested to the percentage increase in the trunk circumference of the grape not infected with grapevine ESCA disease is smaller than 1 (first determination step).

In determining that a grape to be tested is infected with grapevine ESCA disease, the ratio of the percentage increase in the trunk circumference of the grape to be tested to the percentage increase in the trunk circumference of the grape not infected with grapevine ESCA disease is preferably 0.9 or less, more preferably 0.8 or less, and further preferably 0.7 or less. The lower limit value is not particularly limited, and may be, for example, 0 or more, 0.1 or more, 0.3 or more, or 0.5 or more.

The percentage increase (%) in a trunk circumference of a grape can be obtained as a percentage increase in a trunk circumference per year according to a formula "$(((B-A)/A)/C) \times 100$" by measuring: a trunk circumference A of the grape at a certain time point; and a trunk circumference B of the grape after a certain period (C year(s)) elapses since the time point.

The certain period is not particularly limited, but the shorter, the more preferable. The certain period may be, for example, less than 3 years, preferably 2 years or less, more preferably 1.5 years or less, and further preferably 1 year. The lower limit of the period is not particularly limited, either, and can be 6 months or more.

The percentage increase in a trunk circumference of a grape not infected with grapevine ESCA disease may be a percentage increase in a trunk circumference of a single grape, or may be an average value of percentage increases in trunk circumferences of multiple grapes. Preferable is an average value of percentage increases in trunk circumferences of multiple grapes.

The measurement site of a trunk circumference is not particularly limited, but it is preferable to measure a trunk circumference around a predetermined height from the ground (for example, approximately 5 to 10 cm from the ground). Moreover, in a case of a grafted grape, it is preferable to measure a trunk circumference of a relatively smooth portion on a trunk surface, the portion being, for example, approximately 5 to 20 cm away from the grafted portion. In a case of cutting, it is possible to measure a trunk circumference of a portion at a predetermined height from the ground (for example, 5 to 20 cm).

In addition, the grape to be tested and the grape not infected with grapevine ESCA disease are preferably equivalent to each other in conditions such as variety, soil conditions, and growth period.

The method of the present invention makes it possible to determine whether a grape to be tested is infected with grapevine ESCA disease or not even in winter with no leaves.

The above-described identification method of the present invention preferably further includes: a step of applying an agent for controlling grapevine ESCA disease to the grape determined to be infected with grapevine ESCA disease in the first determination step; and a second determination step of comparing a percentage increase in a trunk circumference of the grape after the application of the agent for controlling grapevine ESCA disease and a percentage increase in a trunk circumference of the grape before the application of the agent for controlling grapevine ESCA disease to determine that the grape is infected with grapevine ESCA disease if the ratio of the percentage increase in the trunk circumference of the grape after the application of the agent for controlling grapevine ESCA disease to the percentage increase in the trunk circumference of the grape before the application of the agent for controlling grapevine ESCA disease is 1.1 or more. Including the second determination step enables more reliable determination of whether a grape to be tested is infected with grapevine ESCA disease or not.

The ratio of the percentage increase in the trunk circumference of the grape after the application of the agent for controlling grapevine ESCA disease to the percentage increase in the trunk circumference of the grape before the application of the agent for controlling grapevine ESCA disease is preferably 1.2 or more, more preferably 1.3 or more, and further preferably 1.4 or more. The upper limit value is not particularly limited, and may be, for example, 3.0 or less, 2.0 or less, 1.8 or less, or 1.6 or less.

The agent for controlling grapevine ESCA disease used may be the above-described composition for controlling at least one disease selected from grapevine ESCA disease, grapevine black dead arm, and Eutypa dieback disease of the present invention or the composition for controlling grapevine ESCA disease of the present invention, or other conventionally known agents for controlling grapevine ESCA disease may be used. Among these, the composition for controlling grapevine ESCA disease of the present invention is preferably used.

The use of the identification method of the present invention makes it possible to easily find out a grape infected with grapevine ESCA disease.

After a grape infected with grapevine ESCA disease is identified by using the method of the present invention, other conventionally known agents for controlling grapevine ESCA disease or the composition for controlling grapevine ESCA disease of the present invention can be used to suppress the onset of grapevine ESCA disease symptoms in the identified grape. Alternatively, the identified grape may be pulled out and replaced.

Conventionally, the infection with grapevine ESCA disease has been judged normally by examining changes over time in the percentage of diseased plants, the disease severity of shoots, lengths of shoots elongated, yield, and so forth. However, as described above, since all the branches of a grape except for some main branches are pruned during the dormancy, if a trunk portion near the remaining main branches is not infected with grapevine ESCA disease, the grapevine ESCA disease symptoms may not appear in the grape in the next year. Hence, to accurately evaluate whether an individual grape is infected with grapevine ESCA disease or not, a follow-up examination is required for a long period, specifically at least three years.

On the other hand, it has been found out that the percentage increase in a trunk circumference of a grape infected with grapevine ESCA disease is consistently low in comparison with the percentage increase in a trunk circumference of a grape not infected therewith. The present invention makes it possible to evaluate whether a grape to be tested is infected with grapevine ESCA disease or not within a period shorter than three years by comparing a percentage increase in a trunk circumference of the grape to be tested and a percentage increase in a trunk circumference of a grape not infected with grapevine ESCA disease. More specifically, the evaluation is possible within approximately two years, preferably approximately one to two years.

Another embodiment of the present invention is a method for identifying a grape infected with grapevine ESCA disease, the method including the step of comparing a percentage increase in a trunk circumference of a grape to be tested to which no agent for controlling grapevine ESCA disease is applied and a percentage increase in a trunk circumference of a grape to which an agent for controlling grapevine ESCA disease is applied to determine whether the grape to be tested is infected with grapevine ESCA disease or not.

If a grape to be tested is infected with grapevine ESCA disease, the percentage increase in a trunk circumference thereof is smaller than the percentage increase in a trunk circumference of a grape to which an agent for controlling grapevine ESCA disease is applied. This enables one to determine whether a grape to be tested is infected with grapevine ESCA disease or not.

Thus, the above identification method is preferably a method for identifying a grape infected with grapevine ESCA disease, the method including the step of comparing a percentage increase in a trunk circumference of a grape to be tested to which no agent for controlling grapevine ESCA disease is applied and a percentage increase in a trunk circumference of a grape to which an agent for controlling grapevine ESCA disease is applied to determine that the grape to be tested is infected with grapevine ESCA disease if the ratio of the percentage increase in the trunk circumference of the grape to be tested to the percentage increase in the trunk circumference of the grape to which the agent for controlling grapevine ESCA disease is applied is 0.9 or less.

In determining that a grape to be tested is infected with grapevine ESCA disease, the ratio of the percentage increase in the trunk circumference of the grape to which no agent for controlling grapevine ESCA disease is applied to the percentage increase in the trunk circumference of the grape to which an agent for controlling grapevine ESCA disease is applied is preferably 0.8 or less, more preferably 0.7 or less, and further preferably 0.65 or less. The lower limit value is not particularly limited, and may be, for example, 0.1 or more, 0.2 or more, 0.3 or more, or 0.4 or more.

The percentage increase (%) in a trunk circumference of a grape can be obtained as a percentage increase in a trunk circumference per year according to the formula "$((B-A)/A)/C) \times 100$" by measuring: a trunk circumference A of the grape at a certain time point; and a trunk circumference B of the grape after a certain period (C year(s)) elapses since the time point.

The certain period is not particularly limited, but the shorter, the more preferable. The certain period may be, for example, less than 3 years, preferably 2 years or less, more preferably 1.5 years or less, and further preferably 1 year.

The lower limit of the period is not particularly limited, either, and can be 6 months or more.

The percentage increase in a trunk circumference of a grape to which an agent for controlling grapevine ESCA disease is applied may be a percentage increase in a trunk circumference of a single grape, or may be an average value of percentage increases in trunk circumferences of multiple grapes. Preferable is an average value of percentage increases in trunk circumferences of multiple grapes.

The agent for controlling grapevine ESCA disease used may be the above-described composition for controlling at least one disease selected from grapevine ESCA disease, grapevine black dead arm, and Eutypa dieback disease of the present invention or the composition for controlling grapevine ESCA disease of the present invention, or other conventionally known agents for controlling grapevine ESCA disease may be used. Among these, the composition for controlling grapevine ESCA disease of the present invention is preferably used.

The method of the present invention makes it possible to evaluate whether a grape to be tested is infected with grapevine ESCA disease or not within a shorter time than conventional methods. Moreover, it is possible to determine whether a grape to be tested is infected with grapevine ESCA disease or not even in winter with no leaves.

Another embodiment of the present invention is a searching method for an agent for controlling grapevine ESCA disease, the method including the step of comparing a percentage increase in a trunk circumference of a grape infected with grapevine ESCA disease to which a compound or composition to be tested is applied and a percentage increase in a trunk circumference of a grape infected with grapevine ESCA disease to which no compound or composition to be tested is applied to determine whether the compound or composition to be tested is an agent for controlling grapevine ESCA disease or not.

If a compound or composition to be tested has a control action against grapevine ESCA disease, the percentage increase in a trunk circumference of a grape to which this compound or composition is applied is larger than the percentage increase in a trunk circumference of a grape infected with grapevine ESCA disease to which no compound or composition to be tested is applied. This enables one to determine whether a compound or composition to be tested is an agent for controlling grapevine ESCA disease or not.

Thus, the above searching method is preferably a searching method for an agent for controlling grapevine ESCA disease, the method including the step of comparing a percentage increase in a trunk circumference of a grape infected with grapevine ESCA disease to which a compound or composition to be tested is applied and a percentage increase in a trunk circumference of a grape infected with grapevine ESCA disease to which no compound or composition to be tested is applied (non-treated) to determine that the compound or composition to be tested is an agent for controlling grapevine ESCA disease if the ratio of the percentage increase in the trunk circumference of the grape infected with grapevine ESCA disease to which the compound or composition to be tested is applied to the percentage increase in the trunk circumference of the grape infected with grapevine ESCA disease to which no compound or composition to be tested is applied is larger than 1.

The present invention makes it possible to evaluate whether a compound or composition to be tested is an agent for controlling grapevine ESCA disease having a control action against grapevine ESCA disease or not within a shorter time than conventional methods, more specifically, approximately two years, preferably approximately one to two years.

The ratio of the percentage increase in the trunk circumference of the grape (A) infected with grapevine ESCA disease to which the compound or composition to be tested is applied to the percentage increase in the trunk circumference of the grape infected with grapevine ESCA disease to which no compound or composition to be tested is applied is preferably 1.1 or more, more preferably 1.2 or more, further preferably 1.3 or more, and furthermore preferably 1.4 or more. The upper limit value is not particularly limited, and may be, for example, 3.0 or less, 2.0 or less, 1.8 or less, or 1.6 or less.

The percentage increase (%) in a trunk circumference of a grape can be obtained as a percentage increase in a trunk circumference per year according to the formula "$(((B-A)/A)/C) \times 100$" by measuring: a trunk circumference A of the grape at a certain time point; and a trunk circumference B of the grape after a certain period (C year(s)) elapses since the time point.

The certain period is not particularly limited, but the shorter, the more preferable. The certain period may be, for example, less than 3 years, preferably 2 years or less, more preferably 1.5 years or less, and further preferably 1 year. The lower limit of the period is not particularly limited, either, and can be 6 months or more.

The percentage increase in a trunk circumference of a grape infected with grapevine ESCA disease to which no compound or composition to be tested is applied may be a percentage increase in a trunk circumference of a single grape, or may be an average value of percentage increases in trunk circumferences of multiple grapes. Preferable is an average value of percentage increases in trunk circumferences of multiple grapes.

Examples of the control action against grapevine ESCA disease includes an action having a microbicidal effect and/or a microbiostatic effect against the pathogen of grapevine ESCA disease, an action capable of suppressing the onset of symptoms specific to grapevine ESCA disease, and/or an action capable of reducing the proportion of grapes having grapevine ESCA disease. Among these, preferable is an action capable of suppressing the onset of grapevine ESCA disease symptoms.

The method of the present invention makes it possible to determine whether a compound or composition to be tested is an agent for controlling grapevine ESCA disease or not even in winter with no leaves.

In the identification method and the searching method of the present invention, the percentage increases in trunk circumferences can be evaluated in combination with indicators of other percentage increases, such as a percentage increase in the number of shoots, a percentage increase in lengths of shoots elongated, and so forth. This enables more accurate identification of a grape infected with grapevine ESCA disease and searching for an agent for controlling grapevine ESCA disease.

Desired embodiments of the present invention will be described below.

[1] A composition for controlling grapevine ESCA disease, the composition comprising at least one selected from the group consisting of alkali metal carbonates and alkali metal hydrogen carbonates as an active ingredient.

[2] The composition for controlling grapevine ESCA disease according to [1], wherein the alkali metal is potassium or sodium.

[3] The composition for controlling grapevine ESCA disease according to [1] or [2], further comprising a surfactant.

[4] The composition for controlling grapevine ESCA disease according to [3], wherein the surfactant includes a nonionic surfactant.

[5] The composition for controlling grapevine ESCA disease according to [4], wherein the nonionic surfactant is at least one selected from the group consisting of polyglycerin fatty acid ($C_{8-18}$) esters, polyoxyethylene ($C_{8-18}$) alkyl ethers, polyoxyethylene sorbitan fatty acid ($C_{8-18}$) esters, and polyoxyethylene alkylamines.

[6] The composition for controlling grapevine ESCA disease according to any one of [1] to [5], further comprising a vegetable oil.

[7] The composition for controlling grapevine ESCA disease according to [6], wherein the vegetable oil is soybean oil or sunflower oil.

[8] A package comprising the composition for controlling grapevine ESCA disease according to any one of [1] to [7] packaged in a water soluble film.

[9] The package according to [8], wherein a material of the water soluble film is polyvinyl alcohol.

[10] A method for controlling grapevine ESCA disease, the method comprising applying the composition for controlling grapevine ESCA disease according to any one of [1] to [7] to a grape.

[11] The method for controlling grapevine ESCA disease according to [10], wherein the composition for controlling grapevine ESCA disease according to any one of [1] to [7] is applied to a grape such that an amount of at least one selected from the group consisting of alkali metal carbonates and alkali metal hydrogen carbonates is within a range from 0.01 kg/ha to 1000 kg/ha.

[12] A method for identifying a grape infected with grapevine ESCA disease, the method comprising the step of comparing a percentage increase in a trunk circumference of a grape to be tested and a percentage increase in a trunk circumference of a grape not infected with grapevine ESCA disease to determine whether the grape to be tested is infected with grapevine ESCA disease or not.

[13] A method for identifying a grape infected with grapevine ESCA disease, the method comprising the step of comparing a percentage increase in a trunk circumference of a grape to be tested to which no agent for controlling grapevine ESCA disease is applied and a percentage increase in a trunk circumference of a grape to which an agent for controlling grapevine ESCA disease is applied to determine whether the grape to be tested is infected with grapevine ESCA disease or not.

[14] The identification method according to [13], wherein the agent for controlling grapevine ESCA disease is the composition for controlling grapevine ESCA disease according to any one of [1] to [7].

[15] A searching method for an agent for controlling grapevine ESCA disease, the method comprising the step of comparing a percentage increase in a trunk circumference of a grape infected with grapevine ESCA disease to which a compound or composition to be tested is applied and a percentage increase in a trunk circumference of a grape infected with grapevine ESCA disease to which no compound or composition to be tested is applied to determine whether the compound or composition to be tested is an agent for controlling grapevine ESCA disease or not.

[16] Use of at least one selected from the group consisting of alkali metal carbonates and alkali metal hydrogen carbonates to control grapevine ESCA disease.

[17] The use according to [16], wherein the alkali metal is potassium or sodium.

[18] Use of a composition comprising at least one selected from the group consisting of alkali metal carbonates and alkali metal hydrogen carbonates to control grapevine ESCA disease.

[19] The use according to [18], wherein the alkali metal is potassium or sodium.

[1'] A composition for controlling at least one disease selected from grapevine ESCA disease, grapevine black dead arm, and Eutypa dieback disease, the composition comprising at least one selected from the group consisting of alkali metal carbonates and alkali metal hydrogen carbonates as an active ingredient.

[2'] The composition according to [1'], wherein the disease is grapevine ESCA disease.

[3'] The composition according to [1'] or [2'], wherein the alkali metal is potassium or sodium.

[4'] The composition according to any one of [1'] to [3'], further comprising a surfactant.

[5'] The composition according to [4'], wherein the surfactant includes a nonionic surfactant.

[6'] The composition according to [5'], wherein the nonionic surfactant is at least one selected from the group consisting of polyglycerin fatty acid ($C_{8-18}$) esters, polyoxyethylene ($C_{8-18}$) alkyl ethers, polyoxyethylene sorbitan fatty acid ($C_{8-18}$) esters, and polyoxyethylene alkylamines.

[7'] The composition according to any one of [1'] to [6'], further comprising a vegetable oil.

[8'] The composition according to [7'], wherein the vegetable oil is soybean oil or sunflower oil.

[9'] A package comprising the composition according to any one of [1'] to [8'] packaged in a water soluble film.

[10'] The package according to [9'], wherein a material of the water soluble film is polyvinyl alcohol.

[11'] A method for controlling at least one disease selected from grapevine ESCA disease, black dead arm, and Eutypa dieback disease, the method comprising applying the composition according to any one of [1'] to [8'] to a grape.

[12'] The control method according to [11'], wherein the disease is grapevine ESCA disease.

[13'] The control method according to [11'] or [12'], wherein the composition according to any one of [1'] to [8'] is applied to a grape such that an amount of at least one selected from the group consisting of alkali metal carbonates and alkali metal hydrogen carbonates is within a range from 0.01 kg/ha to 1000 kg/ha.

[14'] A method for identifying a grape infected with grapevine ESCA disease, the method comprising the step of comparing a percentage increase in a trunk circumference of a grape to be tested and a percentage increase in a trunk circumference of a grape not infected with grapevine ESCA disease to determine whether the grape to be tested is infected with grapevine ESCA disease or not.

[15'] A method for identifying a grape infected with grapevine ESCA disease, the method comprising the step of comparing a percentage increase in a trunk circumference of a grape to be tested to which no agent for controlling grapevine ESCA disease is applied and a percentage increase in a trunk circumference of a grape to which an agent for controlling grapevine ESCA disease is applied to determine whether the grape to be tested is infected with grapevine ESCA disease or not.

[16'] The identification method according to [15'], wherein the agent for controlling grapevine ESCA disease is the composition according to any one of [1'] to [8'].

[17'] A searching method for an agent for controlling grapevine ESCA disease, the method comprising the step of comparing a percentage increase in a trunk circumference of a grape infected with grapevine ESCA disease to which a compound or composition to be tested is applied and a percentage increase in a trunk circumference of a grape infected with grapevine ESCA disease to which no compound or composition to be tested is applied to determine whether the compound or composition to be tested is an agent for controlling grapevine ESCA disease or not.

[18'] Use of at least one selected from the group consisting of alkali metal carbonates and alkali metal hydrogen carbonates to control at least one disease selected from grapevine ESCA disease, grapevine black dead arm, and Eutypa dieback disease.

[19'] The use according to [18'], wherein the disease is grapevine ESCA disease.

[20'] The use according to [18'] or [19'], wherein the alkali metal is potassium or sodium.

[21'] Use of a composition comprising at least one selected from the group consisting of alkali metal carbonates and alkali metal hydrogen carbonates to control at least one disease selected from grapevine ESCA disease, grapevine black dead arm disease, and Eutypa dieback disease.

[22'] The use according to [21'], wherein the disease is grapevine ESCA disease.

[23'] The use according to [21'] or [22'], wherein the alkali metal is potassium or sodium.

EXAMPLES

Next, Test Examples according to the present invention will be described. However, the present invention is not limited to these.

Example 1

(1) Potassium hydrogen carbonate (particle diameter; sieve opening of 0.125 to 1.7 mm (115 to 10 mesh/Tyler)), 83% by mass
(2) Soybean oil, 4% by mass
(3) Poem DO-100V (product name, diglycerin monooleate), 4% by mass
(3) Rikemal B-205 (product name, polyoxyethylene lauryl ether), 4% by mass
(3) Sorbon T-20 (product name, polyoxyethylene sorbitan monolaurate), 4% by mass
(3) Sorpol 7643 (product name, polyoxyethylene cocoamine), 1% by mass Potassium hydrogen carbonate having been ground using a centrifugal mill was mixed with all the other ingredients having been heated to 60° C. Thus, the composition of the present invention was obtained.

Example 2

(1) Potassium carbonate (particle diameter; sieve opening of 0.09 to 1.0 mm (170 to 16 mesh/Tyler)), 77% by mass
(2) Sunflower oil, 18% by mass
(2) Soybean oil, 2% by mass
(3) Rikemal B-205 (product name, polyoxyethylene lauryl ether), 0.5% by mass
(3) Sorbon T-20 (product name, polyoxyethylene sorbitan monolaurate), 2% by mass
(3) Sorpol 7643 (product name, polyoxyethylene cocoamine), 0.5% by mass Potassium carbonate having been ground using a centrifugal mill was mixed with all the other ingredients having been heated to 60° C. Thus, the composition of the present invention was obtained.

Example 3

(1) Sodium hydrogen carbonate (particle diameter; sieve opening of 0.045 to 0.15 mm (325 to 100 mesh/Tyler)), 90% by mass
(2) Soybean oil, 3.5% by mass
(3) Poem DO-100V (product name, diglycerin monooleate), 3.5% by mass
(3) Rikemal B-205 (product name, polyoxyethylene lauryl ether), 1% by mass
(3) Sorbon T-20 (product name, polyoxyethylene sorbitan monolaurate), 1% by mass
(3) Sorpol 7643 (product name, polyoxyethylene cocoamine), 1% by mass Sodium hydrogen carbonate having been ground using a centrifugal mill was mixed with all the other ingredients having been heated to 60° C. Thus, the control composition of the present invention was obtained.

Example 4

The control composition of the present invention, 20 g, obtained in Example 1 was filled into a bag made of KURARAY water-soluble Poval Film VF-HP #4000 (product name, made of polyvinyl alcohol, film thickness: approximately 40 μm, length: 6 cm, width: 7 cm, manufactured by Kuraray Co., Ltd.), and the opening was heat-sealed. Thus, a water soluble pack was obtained.

Example 5

The control composition of the present invention, 20 g, obtained in Example 1 was filled into a bag made of a water soluble film Hi-Selon S-660 (product name, made of polyvinyl alcohol, film thickness: approximately 50 μm, length: 6 cm, width: 7 cm, manufactured by The Nippon Synthetic Chemical Industry Co., Ltd.), and the opening was heat-sealed. Thus, a water soluble pack was obtained.

Example 6

The control composition of the present invention, 1000 g, obtained in Example 1 was filled into a bag made of MonoDose M-8534 (product name, made of polyvinyl alcohol, film thickness: approximately 50 μm, length: 18 cm, width: 21 cm, manufactured by Monosol), and the opening was heat-sealed. Thus, a water soluble pack was obtained.

Example 7

(1) Potassium hydrogen carbonate (particle diameter; sieve opening of 0.125 to 1.7 mm (115 to 10 mesh/Tyler)), 83.2% by mass
(2) Soybean oil, 4.2% by mass
(3) Poem DO-100V (product name, diglycerin monooleate), 4.2% by mass
(3) Rikemal B-205 (product name, polyoxyethylene lauryl ether), 4.2% by mass
(3) Sorbon T-20 (product name, polyoxyethylene sorbitan monolaurate), 4.2% by mass Potassium hydrogen carbonate having been ground using a centrifugal mill was mixed with all the other ingredients having been heated to 60° C. Thus, the composition of the present invention was obtained.

Test Example 1

Test Field: ESCA disease-infected field (France)
Tested Variety: wine grape (Cabernet Franc, planted in 1978)
Test Scale: 500 to 550 plants per plot (no replication)
Test Chemical: the potassium carbonate composition of Example 2
Treatment Method: a solution was prepared by diluting the chemical 60-fold with water such that the amount of water applied and the amount of the active ingredient introduced would be 600 L/ha and 10 kg/ha, respectively. The solution was applied mainly on canes, leaves and trunks in a bunch zone by using a power sprayer before and after the optimum harvest date (from the beginning to the middle of October), that is, one and two weeks before the harvest as well as one week after the harvest (three times in total) every year.
Examination Method: before the treatment (in 2012) and one year (in 2013) and two years (in 2014) after the treatment was started, the percentage of diseased plants and the diseased proportion were examined.
Percentage of Diseased Plants: calculated according to the following formula.

Percentage of diseased plants=(the number of grape plants from which leaf discoloration due to grapevine ESCA disease was observed/the number of plants examined)×100

Diseased Proportion: the proportion of leaves discolored due to grapevine ESCA disease in all leaves in the upper part of each grape plant was evaluated from 0: a state where no leaf was discolored in the upper part of the plant to 100: a state where all the leaves were discolored. An average value thereof was regarded as the diseased proportion.
Table 1 shows the result.

TABLE 1

|  | Percentage (%) of diseased plants | | | Diseased proportion | | |
| --- | --- | --- | --- | --- | --- | --- |
|  | before treatment | 1 year later | 2 years later | before treatment | 1 year later | 2 years later |
| Treated plot (with the composition containing potassium carbonate of Example 2) | 24 | 22 | 21 | 18 | 15 | 13 |
| Untreated plot | 22 | 26 | 30 | 16 | 16 | 18 |

In the table, the numbers indicate average values of the examined plants (500 to 550 plants) in each plot In the untreated plot, both the percentage of diseased plants and the diseased proportion tended to increase.

Meanwhile, in the plot treated with the potassium carbonate composition of the present invention, both the percentage of diseased plants and the diseased proportion tended to decrease, and the effect of suppressing the symptom onset was observed.

Test Example 2

Test Field: ESCA disease-infected field (France)
Tested Variety: wine grape (Cabernet Sauvignon, planted in 2002)
Test Scale: 40 plants in the treated plot, 39 plants in the untreated plot (no replication)
Test Chemical: the potassium carbonate composition of Example 2
Treatment Method: the same as that in Test Example 1
Examination Method: every year, the trunk circumference of the narrowest trunk portion approximately 10 cm from the ground was measured before the first applying to calculate a percentage increase since the start of the treatment. Note that, herein, percentage increases in two years were determined. Moreover, from the determined percentage increases in two years, percentage increases per year were calculated.

Percentage increase in two years=(trunk circumference after 2 years since the treatment−trunk circumference before the treatment)/trunk circumference before the treatment×100

TABLE 2

|  | Percentage increase (%) in two years (percentage increase (%) per year) | | The number of plants examined | |
| --- | --- | --- | --- | --- |
|  | healthy plant | infected plant | healthy plant | infected plant |
| Treated plot (with the composition containing potassium carbonate of Example 2) | 9.2 (4.6) | 8.8 (4.4) | 14 | 26 |
| Untreated plot | 9.0 (4.5) | 6.2 (3.1) | 7 | 32 |

Healthy plant: grape having no the ESCA disease symptom (leaf discoloration symptom specific to the subject disease) even once during the test period (two years)
Infected plant: grape having the ESCA disease symptom on the leaves once or more during the test period (two years)

In the plot treated with the potassium carbonate composition of the present invention, the effect of suppressing the symptom onset was observed as in Test Example 1. Further, the percentage increases in the trunk circumferences were compared between the treated plot of the present invention and the untreated plot. Between the healthy plants in both the plots, there was very little difference in the percentage increases in the trunk circumferences. Meanwhile, between the infected plants, the percentage increase in the trunk circumference in the plot treated with the potassium carbonate composition was apparently larger than that in the untreated plot.

Test Example 3

Test Field: ESCA disease-infected field (France)
Tested Variety: wine grape (Cabernet Sauvignon, planted in 2002)
Test Scale: 166 plants/one treated plot, 34 plants/one untreated plot (no replication)
Test Chemical: the potassium hydrogen carbonate composition of Example 1
Treatment Method: the same as that in Test Example 1 (the examination before the treatment was performed in 2013)

Examination Method: the same as that in Test Example 2 (however, the percentage increases are percentage increases in one year.)

TABLE 3

|  | Percentage increase (%) in one year | | The number of plants examined | |
| --- | --- | --- | --- | --- |
|  | healthy plant | infected plant | healthy plant | infected plant |
| Treated plot (with the composition containing potassium hydrogen carbonate of Example 1) | 7.0 | 5.9 | 59 | 107 |
| Untreated plot | 6.7 | 3.8 | 16 | 18 |

Healthy plant: grape having no the ESCA disease symptom even once during the test period (one year)
Infected plant: grape having the symptom on the leaves once or more during the test period (one year)

In the plot treated with the potassium hydrogen carbonate composition of the present invention, the effect of suppressing the symptom onset was observed as in Test Example 1. Further, the percentage increases in the trunk circumferences were compared between the treated plot of the present invention and the untreated plot. Between the healthy plants in both the plots, there was very little difference in the percentage increases in the trunk circumferences. Meanwhile, between the infected plants, the percentage increase in the trunk circumference in the plot treated with the potassium hydrogen carbonate composition was apparently larger than that in the untreated plot.

Further, the examination period for the grapes of Test Example 3 was extended for one year to examine a correlation between the diseased leaf proportion and the trunk circumference in each of the treated plot and the untreated plot from 2013 to 2015. As a result, as shown in Table 4 below, in the untreated plot, a correlation was observed such that a higher diseased leaf proportion leads to a smaller trunk circumference. Meanwhile, in the treated plot, the trunk circumference continued to increase regardless of the diseased leaf proportion.

TABLE 4

|  | Slope of approximate straight line | | |
| --- | --- | --- | --- |
|  | 2013 | 2014 | 2015 |
| Treated plot (with the composition containing potassium hydrogen carbonate of Example 1) | 0.0031 | 0.0039 | 0.0087 |
| Untreated plot | −0.0084 | −0.009 | −0.0024 |

The diseased leaf proportions and the trunk circumferences of all the examined plants for each year were plotted on the X axis and the Y axis, respectively. From the approximate straight lines obtained therefrom, the slopes were determined.

The results of Test Examples 2 and 3 revealed that the infected plants had smaller percentage increases in the trunk circumferences than the healthy plants, and that the presence or absence of the symptom onset was correlated with the percentage increase in the trunk circumference. Thus, it was found out that a percentage increase in a trunk circumference can be utilized as an indicator for identifying a grape infected with grapevine ESCA disease.

Moreover, it was revealed that there was very little difference in the percentage increases in the trunk circumferences of the healthy plants between the treated plot and the untreated plot, and that the composition for controlling grapevine ESCA disease capable of reducing the percentage of diseased plants and the diseased proportion (Test Example 1) hardly influenced the percentage increases in the trunk circumferences of the healthy plants. On the other hand, it was revealed from the infected plants that increases in the trunk circumferences were observed as a result of applying the compositions of the present invention, and that the compositions for controlling grapevine ESCA disease greatly influenced the percentage increases in the trunk circumferences of the infected plants. From the foregoing, it was found out that a percentage increase in a trunk circumference can be utilized as an indicator for searching for a novel ESCA disease control agent.

Test Example 4

Test for Effect of Inhibiting Mycelial Growth of Grapevine ESCA Disease Pathogens Tested Fungi: *Phaeomoniella chlamydospora, Phaeoacremonium aleophilum, Fomitiporia mediterranea*

Tested Chemicals: the composition containing potassium hydrogen carbonate of Example 1 or the composition containing potassium hydrogen carbonate of Example 7

To a PDA medium containing the composition containing potassium hydrogen carbonate of Example 1 or the composition containing potassium hydrogen carbonate of Example 7 at a predetermined concentration (ppm based on mass/volume), a colony (diameter: 4 mm) obtained by preculturing was transferred and cultured at room temperature (20 to 25° C.) for 3 days. Then, the diameter of the colony thus grown was measured, and a percentage inhibition (%) of mycelial growth was determined based on the following formula.

Percentage inhibition (%) of mycelial growth=$(1-a/b) \times 100$ a: colony diameter in the treated plot, b: colony diameter in the untreated plot Tables 5 and 6 show the results.

TABLE 5

Effect of inhibiting mycelial growth of ESCA disease pathogens by the composition containing potassium hydrogen carbonate of Example 1

|  | Percentage inhibition (%) of mycelial growth | | |
| --- | --- | --- | --- |
| Tested pathogen | 10000 ppm | 5000 ppm | 2000 ppm |
| *Phaeomoniella chlamydospora* | 100 | 100 | 57.1 |
| *Phaeoacremonium aleophilum* | 100 | 84.8 | 39.4 |
| *Fomitiporia mediterranea* | 83.1 | 75.8 | 56.6 |

TABLE 6

Effect of inhibiting mycelial growth of ESCA disease pathogens by the composition containing potassium hydrogen carbonate of Example 7

| Tested pathogen | Percentage inhibition (%) of mycelial growth | | |
|---|---|---|---|
| | 10000 ppm | 5000 ppm | 2000 ppm |
| *Phaeomoniella chlamydospora* | 100 | 100 | 62.9 |
| *Phaeoacremonium aleophilum* | 86.4 | 59.1 | 24.2 |
| *Fomitiporia mediterranea* | 81.8 | 75.8 | 60.0 |

Test Example 5

Test for Effect of Inhibiting Mycelial Growth of Grapevine Black Dead Arm Pathogen
Tested Fungus: *Botryosphaeria parva*
Tested Chemical: the composition containing potassium hydrogen carbonate of Example 1

To a PDA medium containing the composition containing potassium hydrogen carbonate of Example 1 at a predetermined concentration (ppm based on mass/volume), a colony (diameter: 4 mm) obtained by preculturing was transferred and cultured at room temperature (20 to 25° C.) for 3 days. Then, the diameter of the colony thus grown was measured, and a percentage inhibition (%) of mycelial growth was determined based on the following formula.

Percentage inhibition (%) of mycelial growth=$(1-a/b) \times 100$ a: colony diameter in the treated plot, b: colony diameter in the untreated plot
Table 7 shows the result.

TABLE 7

| Percentage inhibition (%) of mycelial growth | | |
|---|---|---|
| 10000 ppm | 5000 ppm | 2000 ppm |
| 100 | 100 | 100 |

Test Example 6

Test for Effect of Inhibiting Mycelial Growth of Grapevine Eutypa Dieback Disease Pathogen
Tested Fungus: *Eutypa lata*
Tested Chemicals: the composition containing potassium hydrogen carbonate of Example 1 or the composition containing potassium hydrogen carbonate of Example 7

To a PDA medium containing the composition containing potassium hydrogen carbonate of Example 1 or the composition containing potassium hydrogen carbonate of Example 7 at a predetermined concentration (ppm based on mass/volume), a colony (diameter: 4 mm) obtained by preculturing was transferred and cultured at room temperature (20 to 25° C.) for 3 days. Then, the diameter of the colony thus grown was measured, and a percentage inhibition (%) of mycelial growth was determined based on the following formula.

Percentage inhibition (%) of mycelial growth=$(1-a/b) \times 100$ a: colony diameter in the treated plot, b: colony diameter in the untreated plot Table 8 shows the results.

TABLE 8

| | Percentage inhibition (%) of mycelial growth | | |
|---|---|---|---|
| | 10000 ppm | 5000 ppm | 2000 ppm |
| Composition containing potassium hydrogen carbonate of Example 1 | 100 | 100 | 100 |
| Composition containing potassium hydrogen carbonate of Example 7 | 100 | 100 | 100 |

This Description includes the contents described in the description and/or the scope of claims of Japanese Patent Application No. 2015-101136, based on which the present application claims priority. In addition, all the publications, patent, and patent applications cited herein are incorporated herein by reference in their entirety.

INDUSTRIAL APPLICABILITY

The control composition and the control method of the present invention are very safe for the environment and the worker, and make it possible to suppress the onset of grapevine ESCA disease symptoms. Moreover, the identification method of the present invention makes it possible to identify a grape infected with grapevine ESCA disease within a shorter time than conventional methods. Further, the searching method of the present invention makes it possible to find out a chemical effective against grapevine ESCA disease by a simple process. In addition, the control composition and the control method of the present invention are very safe for the environment and the worker, and make it possible to suppress the onset of symptoms of at least one disease selected from grapevine ESCA disease, grapevine black dead arm, and Eutypa dieback disease. Therefore, the control composition and the control method of the present invention are industrially quite useful.

The invention claimed is:

1. A method for controlling at least one disease selected from grapevine ESCA disease, black dead arm disease, and Eutypa dieback disease, the method comprising applying to a grape a composition comprising potassium carbonate as an active ingredient.

2. The control method according to claim 1, wherein the disease is grapevine ESCA disease.

3. The control method according to claim 1, wherein the composition is applied to a grape such that an amount of potassium carbonate is within a range from 0.01 kg/ha to 1000 kg/ha.

4. The control method according to claim 1, wherein the composition further comprises a surfactant.

5. The control method according to claim 4, wherein the surfactant comprises a nonionic surfactant.

6. The control method according to claim 5, wherein the nonionic surfactant is at least one selected from the group consisting of polyglycerin fatty acid ($C_{8-18}$) esters, polyoxyethylene ($C_{8-18}$) alkyl ethers, polyoxyethylene sorbitan fatty acid ($C_{8-18}$) esters, and polyoxyethylene alkylamines.

7. The control method according to claim 1, wherein the composition further comprises a vegetable oil.

8. The control method according to claim 7, wherein the vegetable oil is soybean oil or sunflower oil.

9. The control method according to claim 1, wherein the composition is applied to a grape within a period between eight weeks before the harvest and eight weeks after the harvest.

10. The control method according to claim 1, wherein the composition is applied to a grape within a period between four weeks before the harvest and four weeks after the harvest.

11. The control method according to claim 1, wherein the disease is black dead arm disease.

12. The control method according to claim 1, wherein the disease is Eutypa dieback disease.

13. The control method according to claim 1, wherein the composition is applied to a grape which is infected with grapevine ESCA disease.

14. The control method according to claim 2, wherein the composition is applied to a grape which is infected with grapevine ESCA disease.

* * * * *